US010039507B2

(12) United States Patent
Patil et al.

(10) Patent No.: US 10,039,507 B2
(45) Date of Patent: Aug. 7, 2018

(54) ADVANCED INTRAOPERATIVE NEURAL TARGETING SYSTEM AND METHOD

(71) Applicant: THE REGENTS OF THE UNIVERSITY OF MICHIGAN, Ann Arbor, MI (US)

(72) Inventors: Parag G. Patil, Ann Arbor, MI (US); Sunjay Dodani, Palo Alto, CA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/030,791

(22) Filed: Sep. 18, 2013

(65) Prior Publication Data

US 2014/0081127 A1 Mar. 20, 2014

Related U.S. Application Data

(60) Provisional application No. 61/703,110, filed on Sep. 19, 2012.

(51) Int. Cl.
*A61B 6/12* (2006.01)
*A61B 34/20* (2016.01)
*A61B 34/10* (2016.01)
*A61B 34/30* (2016.01)
(Continued)

(52) U.S. Cl.
CPC .............. *A61B 6/12* (2013.01); *A61B 34/20* (2016.02); *A61B 34/30* (2016.02); *A61B 2034/107* (2016.02); *A61N 1/0529* (2013.01); *A61N 1/36057* (2013.01); *A61N 1/36082* (2013.01)

(58) Field of Classification Search
None
See application file for complete search history.

(56) References Cited

U.S. PATENT DOCUMENTS

| 6,083,252 A | 7/2000 | King et al. |
| 6,109,270 A | 8/2000 | Mah et al. |
| 6,167,311 A | 12/2000 | Rezai |

(Continued)

FOREIGN PATENT DOCUMENTS

| EP | 0 998 958 A2 | 5/2000 |
| EP | 1 062 973 A1 | 12/2000 |

(Continued)

OTHER PUBLICATIONS

Starr, Philip A., et al. "Microelectrode-guided implantation of deep brain stimulators into the globus pallidus internus for dystonia: techniques, electrode locations, and outcomes." Journal of neurosurgery 104.4 (2006): 488-501.*

(Continued)

*Primary Examiner* — Carolyn Pehlke
(74) *Attorney, Agent, or Firm* — Marshall, Gerstein & Borun LLP; Randall G. Rueth

(57) ABSTRACT

A neural targeting system and method for deep brain stimulation procedures, or other types of brain surgeries requiring targeting, provides high spatial resolution and real-time targeting analysis to identify structural boundaries resulting in increased spatial accuracy. The system and method uses quantitative electrophysiology to update static brain images with an actual microelectrode location and trajectory in the brain to ensure correct placement of a later implanted stimulation probe.

20 Claims, 11 Drawing Sheets

(51) Int. Cl.
*A61N 1/05* (2006.01)
*A61N 1/36* (2006.01)

(56) References Cited

U.S. PATENT DOCUMENTS

| | | | |
|---|---|---|---|
| 6,253,109 B1 | 6/2001 | Gielen | |
| 6,343,226 B1 | 1/2002 | Sunde et al. | |
| 6,718,196 B1 | 4/2004 | Mah et al. | |
| 7,369,899 B2 | 5/2008 | Malinowski et al. | |
| 8,108,025 B2 | 1/2012 | Csavoy et al. | |
| 2004/0006274 A1 | 1/2004 | Giller et al. | |
| 2004/0106916 A1* | 6/2004 | Quaid et al. | 606/1 |
| 2005/0004617 A1 | 1/2005 | Dawant et al. | |
| 2005/0171558 A1* | 8/2005 | Abovitz | A61B 90/36 606/130 |
| 2006/0058855 A1 | 3/2006 | Gill | |
| 2006/0190055 A1 | 8/2006 | Malinowski et al. | |
| 2006/0235483 A1* | 10/2006 | Schwan | 607/45 |
| 2008/0081982 A1* | 4/2008 | Simon | G06F 19/3437 600/407 |
| 2009/0118786 A1 | 5/2009 | Meadows et al. | |
| 2009/0220136 A1 | 9/2009 | Bova et al. | |
| 2009/0259230 A1* | 10/2009 | Khadem | A61B 19/5244 606/130 |
| 2009/0318935 A1* | 12/2009 | Sundar et al. | 606/130 |
| 2010/0036468 A1 | 2/2010 | Decre et al. | |
| 2010/0185257 A1 | 7/2010 | Aksenova et al. | |
| 2010/0324410 A1 | 12/2010 | Paek et al. | |
| 2011/0077504 A1* | 3/2011 | Fischer | A61B 34/30 600/411 |
| 2011/0307079 A1 | 12/2011 | Oweiss et al. | |
| 2012/0150256 A1 | 6/2012 | Martens | |

FOREIGN PATENT DOCUMENTS

| | | |
|---|---|---|
| WO | WO-2007/092316 A2 | 8/2007 |
| WO | WO-2011/098937 A1 | 8/2011 |
| WO | WO 2012092511 A2 * | 7/2012 |

OTHER PUBLICATIONS

Gross, Robert E., et al. "Electrophysiological mapping for the implantation of deep brain stimulators for Parkinson's disease and tremor." Movement disorders 21.S14 (2006): S259-S283.*

Kim et al., "Microelectrode Recording-Guided Deep Brain Stimulation in Patients with Movement Disorders," *J Korean Neurosurg Soc*, 31:11-15 (2002).

Collins et al., "Deep Brain Stimulation for Movement Disorders," *Neurobology Disease*, 38:338-45 (2010).

International Search Report and Written Opinion for International application No. PCT/US2013/060367, dated Dec. 23, 2013.

* cited by examiner

FIG. 10

ADVANCED INTRAOPERATIVE NEURAL TARGETING SYSTEM AND METHOD

FIELD OF TECHNOLOGY

The following disclosure relates to systems and methods requiring precise targeting for the treatment of illnesses, for example, neurological diseases and disorders involving, for example, brain tumors, epilepsy, hydrocephalus, movement disorders, pain, spine, radiosurgery, pituitary and neuroendocinology, and cerebral drug delivery.

BACKGROUND

More than 10 million people in the U.S. suffer from movement disorders such as essential tremor, dystonia, and Parkinson's disease. Additionally, over three million people in the U.S. and over 50 million people worldwide suffer from epilepsy. One effective emerging treatment for these diseases is deep brain stimulation (DBS) of the subthalamic nucleus with periodic high-frequency electric pulse trains. DBS therapy has been approved by the U.S. Food and Drug Administration for the treatment of Parkinson's disease, essential tremor, dystonia, and obsessive-compulsive disorder, and is showing signs of promise for the treatment of intractable epilepsy and major depression.

DBS devices apply electrical stimulation to a targeted small region of the brain via an implanted electrode to block corrupted neural signals responsible for disease symptoms. The optimal neural target typically occupies a relatively small volume (several cubic millimeters) deep within the brain, which may be a short distance (2-3 mm) from other structures that could lead to serious side effects if they are damaged, disrupted, or inadvertently stimulated by the electrode in the course of targeting or treatment. The accurate placement of the DBS electrode is critical for achieving an optimal treatment effect from DBS therapy with minimal risk and side effects to the patient in both the long and short term. One factor that may affect the accurate placement of the DBS electrode relates to the shifting of the brain that may occur when the skull is opened after images of the brain have been taken. Another factor that may affect the accurate placement of the DBS electrode relates to image resolution limitations that can include an error range of +/−5 mm. Because anatomical information of the brain attained by computed tomography (CT) and/or magnetic resonance imaging (MRI) devices may be inadequate by itself for defining the best target, functional mapping of the brain is also utilized in DBS surgery.

Functional mapping of the brain involves penetrating computed target structures with a microelectrode to identify the neuronal structural boundaries using electrical activity picked up or received by the tip of the microelectrode. There is sufficient variability among individual functional anatomy and pathological localization to utilize functional (e.g., electrophysiological) information along with anatomical information for target verification in an individual patient. Electrical activity is measured in two main neural potentials: single unit action potentials (SPIKES) and local field potentials (LFP). Neuronal structure boundaries are identified using SPIKES, for example, received by the microelectrode. The measured SPIKES from the microelectrode are analyzed acoustically in real-time by an electrophysiologist to determine if the intended target region has been found. The primary limitation to this standard practice is the subjective identification of the desired target from the brain image. An error in either method may lead to longer surgeries, increased risk to the patient, and if not corrected, a poorly positioned electrode resulting in a negative patient outcome with poor symptom control and potential stimulation side effects.

The technical challenges of targeting electrode placement in the brain are disincentives for general neurosurgeons to perform DBS surgery. Therefore, a clear and unmet need exists to improve the ease and accuracy of DBS surgery, to reduce surgical risk, to increase the speed of DBS procedures, and to allow more general neurosurgeons to perform DBS surgery.

SUMMARY

Described herein are example systems and methods for precisely targeting a location, for example, within a brain. The example systems and methods for targeting a location within the brain may be applied in surgeries involving, but not limited to, brain tumors, epilepsy, hydrocephalus, movement disorders, pain, spine, radiosurgery, pituitary and neuroendocinology, deep brain stimulation, and cerebral drug delivery. One example method identifies a virtual target within an image of the brain, wherein the image includes a plurality of regions and each region includes a hue associated to an electrophysiological activity. The method defines, via one or more processors, a portion of the image into a plurality of virtual paths, wherein each virtual path of the plurality of virtual paths includes a sequence of image segments and at least one virtual path of the plurality of virtual paths extends to the virtual target. The method correlates each image segment of the sequence of image segments of the plurality of virtual paths into an electrophysiological value segment, and transforms the sequence of image segments of each virtual path into a sequence of electrophysiological value segments. The method correlates the virtual target within the image to a physical target in the brain, selects one of the at least one virtual path of the plurality of virtual paths that extends to the virtual target, and correlates the selected one virtual path to a physical path in the brain. The method extends a microelectrode into the brain on the physical path toward the physical target and receives or picks up, via the microelectrode, a plurality of electrophysiological signals as the microelectrode extends on the physical path toward the physical target. The method matches the electrophysiological signals received by the microelectrode on the physical path to the sequence of electrophysiological value segments of a particular virtual path of the plurality of virtual paths and determines whether the physical path on which the microelectrode is travelling will reach the physical target.

If desired, the method may also include calculating a physical location of the microelectrode in the brain with respect to the physical target, wherein the microelectrode is advanced further toward the physical target if the physical location of the microelectrode is determined to be on the physical path to reach the physical target, or an alternate physical path for the microelectrode to the physical target is planned if the physical location of the microelectrode is determined to be off the physical path to reach the physical target. The method may indicate the physical location of the microelectrode by displaying a visual indicator, such as a location on the image of the brain corresponding to the physical location of the microelectrode in the brain, for example, and/or emitting an auditory indicator. Additionally, the method may generate, via a stimulator, an intraoperative stimulation of the microelectrode to identify regions of the brain structure that have an observable response to stimulation in the form of sensations experienced by the individual. Such stimulation can be applied with constant current, custom waveform, variable frequency, variable signal pulse width, and high precision signal amplitude.

In another example embodiment, a system for targeting a location within a brain for deep brain stimulation includes an integrated monitoring system having one or more processors and a microelectrode operatively coupled to the one or more processors, wherein the microelectrode receives or picks up electrophysiological signals of the brain. The system includes a memory operatively coupled to the integrated monitoring system and one or more modules or routines stored on the memory, which when executed on by the processor, may provide high spatial resolution, real-time targeting analysis, and the capability to use microstimulation with neural activity recordings to identify structural boundaries in the brain resulting in increased spatial accuracy. In particular, the system may include an imaging module to define an image of a brain into a plurality of image regions with each image region including a hue associated to an electrophysiological activity; a virtual path generating module to define a plurality of virtual paths through the image, wherein each virtual path of the plurality of virtual paths includes a sequence of image segments, and wherein at least one virtual path of the plurality of virtual paths extends to a virtual target; a transforming module to transform the sequence of the image segments of at least one virtual path of the plurality of virtual paths into a sequence of electrophysiological value segments; an analyzing module to match or compare a sequence of physiological signals received by the microelectrode on the physical path to the sequence of electrophysiological value segments of a particular virtual path of the plurality of virtual paths; a calculating module to utilize the analyzed electrophysiological signals received by the microelectrode on the physical path to determine a location of the microelectrode within the brain; and an indicating module to indicate the location of the microelectrode.

BRIEF DESCRIPTION OF THE DRAWINGS

FIG. 10 is an illustration of voxel values correlated from electrophysiological signals received by the microelectrode along a trajectory in the brain and displayed on a screen.

DETAILED DESCRIPTION

Figure 1:
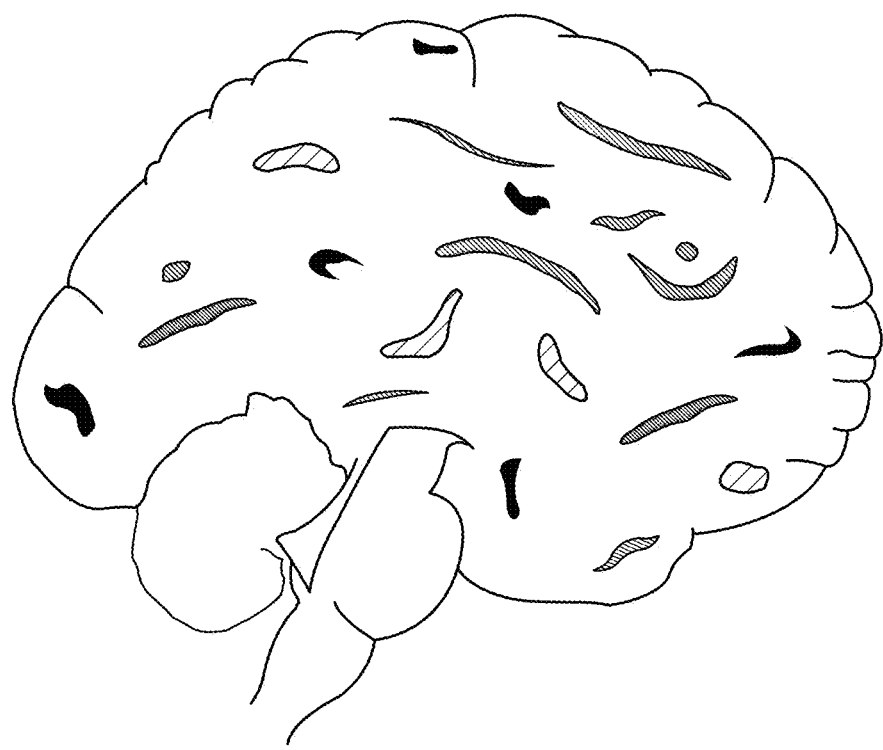
FIG. 1 is a side cross-section view of an MRI image of human brain depicting various regions of electrophysiological activity.

The disclosed system and method may utilize a real-time neural targeting system for intraoperative deep brain stimulation (DBS) procedures to treat various neurological disorders and illnesses, including essential tremor, dystonia, and Parkinson's disease. The neural targeting system may include an intraoperative data acquisition system (IODA) to provide high spatial resolution, targeting analysis, and the capability to use microstimulation with microelectrode recordings to identify structural boundaries of the brain. In general, the neural targeting system and method utilizes quantitative electrophysiology and advanced imaging analysis to identify inaccuracies in a planned target path and target position. A full bandwidth of microelectrode signals relating to the boundaries of brain structures is used to rapidly determine if the planned target position is the actual structure or if an adjustment to the target location is needed. More specifically, a microelectrode located at the tip of a probe inserted into the brain receives or picks up electrical activity within the brain that is used to identify neuronal structural boundaries. The identified boundaries facilitate the finding of target locations faster and more accurately than current methods, which help to ensure accurate placement of a later implanted stimulation probe. In particular, the quantitative relationship that exists between neural electrophysiological activity and MRI images of the brain is utilized to facilitate target selection. Regions of the brain exhibiting neural electrophysiological activity appear more dense in corresponding regions of an MRI image as compared to regions of the brain exhibiting less or no neural electrophysiological activity. These active or dense regions of the MRI image appear in a dark hue or shade on the MRI image while less dense regions of the image appear in a light or relatively lighter shade. These active regions can also be inverted to lighter shades on the image depending on the imaging protocol used. The dark and darker regions generally indicate electrophysiological activity that is measureable greater than light and lighter shaded regions. In FIG. 1, the distinguishable regions of dark and light shades in the MRI image depict structural boundaries in the brain. By utilizing MRI image analysis in conjunction with acquired electrophysiological signals, a highly accurate and functional real-time targeting system can be provided.

Figure 2:
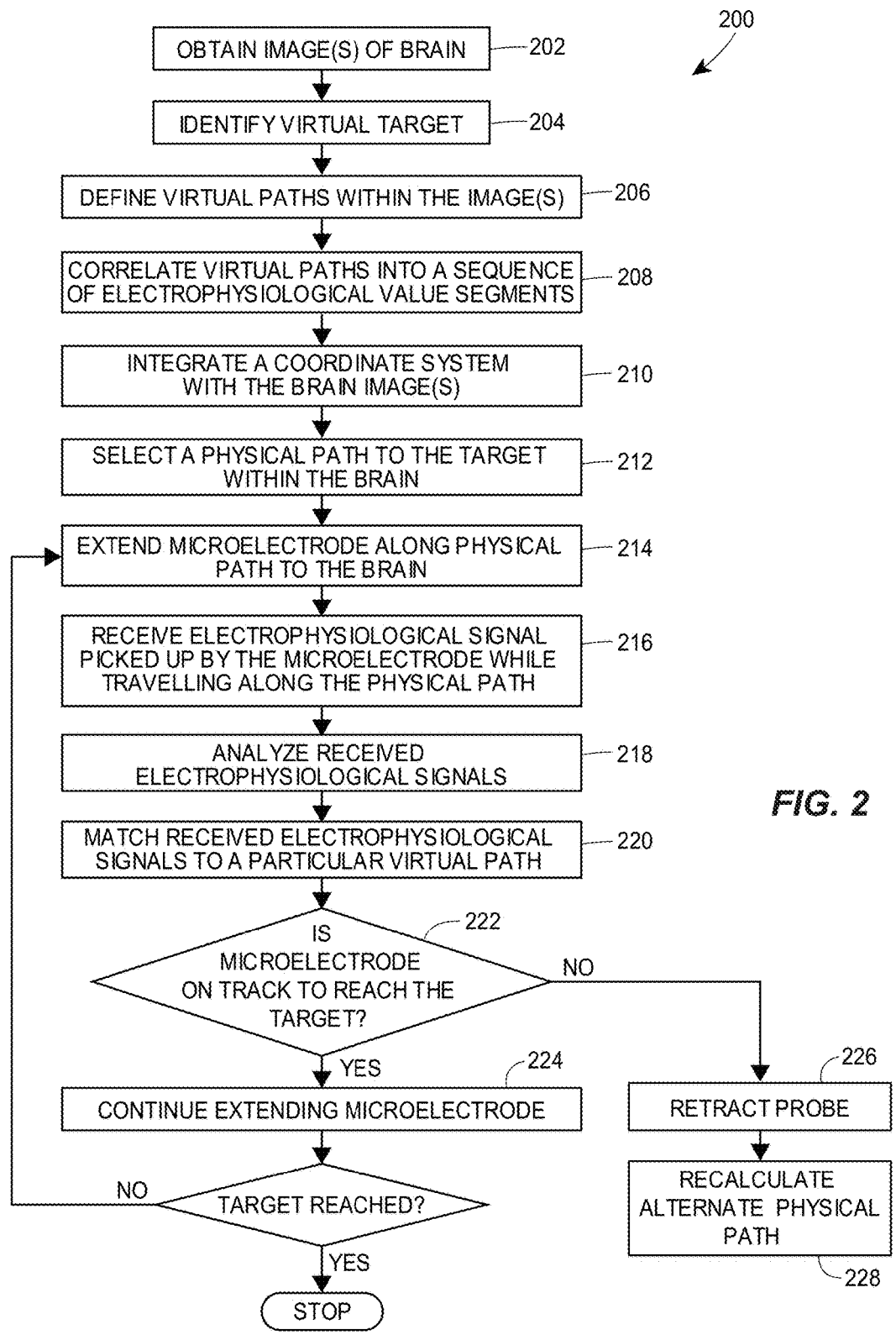
FIG. 2 illustrates a flow diagram of an example module or routine using the neural targeting system assembled in accordance with the teachings of the present invention and used to locate a target in the brain.

A flow diagram of one implementation of an example method 200 for targeting a location within the brain for deep brain stimulation (DBS) is depicted in FIG. 2. Initially, one or more MRI images of an individual's cranium is obtained using an imaging device (block 202). The MRI image may be two or three dimensional, e.g., pixels, voxels; and provides contrast characteristics to distinguish a plurality of regions in the brain by exhibiting a hue, shade, or color associated with the electrophysiological activity or function of each particular region.

A virtual target is identified for later placement of a stimulating probe within the MRI image of the brain (block 204) and a portion of the MRI image is defined into a plurality of virtual paths (block 206). Each virtual path includes a sequence of image segments and at least one virtual path of the plurality of virtual paths extends to the virtual target. Each image segment of the sequence of image segments of the plurality of virtual paths is associated with one of the plurality of regions of the MRI image and is correlated into an electrophysiological value segment (block 208). Each virtual path is thereby transformed to include a sequence of electrophysiological value segments corresponding to the respective sequence of image segments. For example, dark and darker shaded image segments generally correlate into electrophysiological value segments having higher values while light and lighter shaded image segments generally correlate into lower electrophysiological value segments having relatively lower values.

Prior to DBS surgery, the individual's head is placed into a head-frame or ring and a CT scan is taken of the individual's head. The MRI image is then merged, fused, overlaid, etc., with the CT scan image to integrate a coordinate system with the MRI image (block 210). The integrated coordinate system and MRI image(s) enable the user to correlate the virtual target to a physical target within the brain, correlate virtual paths to physical paths, determine an entry point of the microelectrode into the individual's brain, and calculate a safe physical path or trajectory for the microelectrode to the physical target (block 212).

The microelectrode is extended into the brain on a selected physical path toward the physical target (block 214). The microelectrode may be extended into the brain by the surgeon via manual adjustment of the stereotactic frame. Alternatively, the microelectrode may be extended automatically via a robot and/or a robotic system. As the microelectrode extends along the physical path toward the physical target, the microelectrode receives or picks up electrophysiological activity, e.g., a sequence of electrophysiological signals (block 216). A processor analyzes the electrophysiological activity (block 218) and matches the sequence of the electrophysiological signals received by the microelectrode on the physical path to the sequence of electrophysiological value segments of a particular virtual path of the earlier defined plurality of virtual paths (block 220). In particular, the electrophysiological signals received by the microelectrode are compared to the sequence of electrophysiological value segments of the plurality of virtual paths. The processor determines which of the sequences of electrophysiological value segments of the plurality of virtual paths likely coincides with the sequence of electrophysiological signals received by the microelectrode and whether the corresponding physical path will reach the physical target (block 222).

If it is determined that the physical path of the microelectrode will reach the physical target, the microelectrode is further extended toward the physical target (block 224). As the microelectrode is further extended, additional electrophysiological signals are received by the microelectrode, analyzed, and matched with the sequence of electrophysiological value segments of the plurality of virtual paths. As long as the physical path the microelectrode is travelling is determined to coincide with a virtual path that will reach the physical target, the microelectrode will continue to be further extended into the brain until the microelectrode reaches the physical target. However, if it is determined that the physical path the microelectrode is travelling no longer matches a virtual path that reaches the physical target, the microelectrode may be retracted from the brain (block 226) and an alternate physical path may be calculated by the processor (block 228).

The targeting system and method described herein may be particularly advantageous to the user in instances where the brain may have moved in respect to its position at the time the MRI image(s) was taken. For example, prior to the opening of the skull, the MRI image(s) is taken and the virtual path to the virtual target on the MRI image is correlated to the planned physical path to the physical target within the brain. However, when the skull is opened for DBS surgery, the brain may move due to the release of pressure within the skull. This shift of the brain can also occur in other brain related surgeries such as, for example, brain tumor removals, cerebral drug delivery, and surgeries requiring ablation of brain tissue. If the brain does move, the location of the physical target and the planned physical path to the physical target may move. Thus, the planned trajectory of the microelectrode to the physical target may no longer coincide with the planned entry point into the brain and an alternate physical path to the physical target and/or an entry point to the physical path may be need to be calculated.

In one embodiment to calculate an alternate physical path to the physical target for the microelectrode, the processor utilizes the spatial relationships among the coordinates and trajectories of the plurality of virtual paths. More specifically, because the processor defined the plurality of virtual paths, the processor is aware of the coordinates and trajectory of each defined virtual path. The processor is also aware of the electrophysiological values correlated from the brain image(s) that are expected to match the electrophysiological signals received or picked up by the microelectrode moving along each corresponding physical path in the brain. By matching the respective sequences of electrophysiological value segments of the plurality of virtual paths to the sequence of electrophysiological signals received or picked up by the microelectrode while moving toward the physical target, the processor is able to calculate which particular virtual path of the plurality of virtual paths correspond to the physical path the microelectrode is travelling along. Also, because the processor is aware of which virtual paths reach the virtual target, the processor is able to calculate whether the particular virtual path that corresponds to the physical path the microelectrode is moving along will reach the virtual target. If the physical location of the microelectrode corresponds to a virtual path that does not lead to the virtual target, the microelectrode is considered to be off-track and not able to reach the physical target. The off-track microelectrode may be retracted from the brain and aligned with an alternate physical path that corresponds to another virtual path that does reach the virtual target, which will therefore allow the microelectrode to reach the physical target.

In another embodiment to calculate an alternate physical path to the target for the microelectrode, the processor calculates the spatial adjustment needed to reposition the microelectrode by determining the spatial difference between the virtual path corresponding to the physical path the microelectrode is moving along, to a particular virtual path leading to the virtual target. The processor uses the spatial differences between these two defined virtual paths to reposition the microelectrode external to the brain and align the microelectrode with an entry point and trajectory that coincides with an alternate physical path, which corresponds to the particular virtual path that reaches the virtual target, and thus will allow the microelectrode to reach the physical target.

Figure 3:
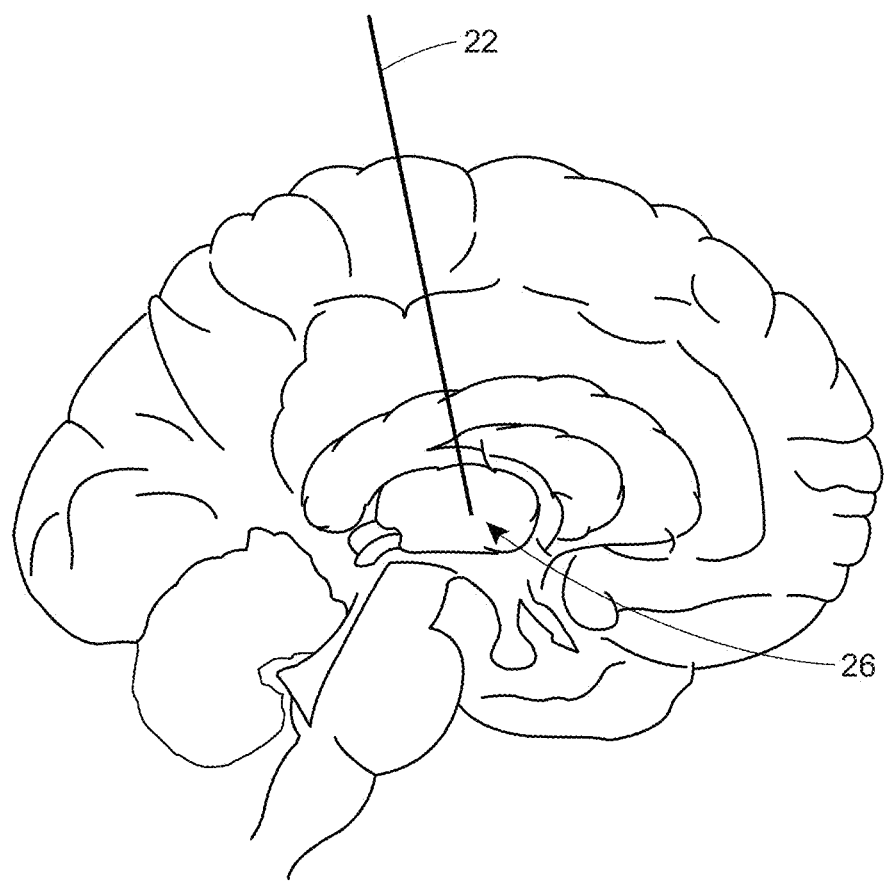
FIG. 3 is an image depicting a side cross-section view of a microelectrode inserted into a human brain.
Figure 4A:
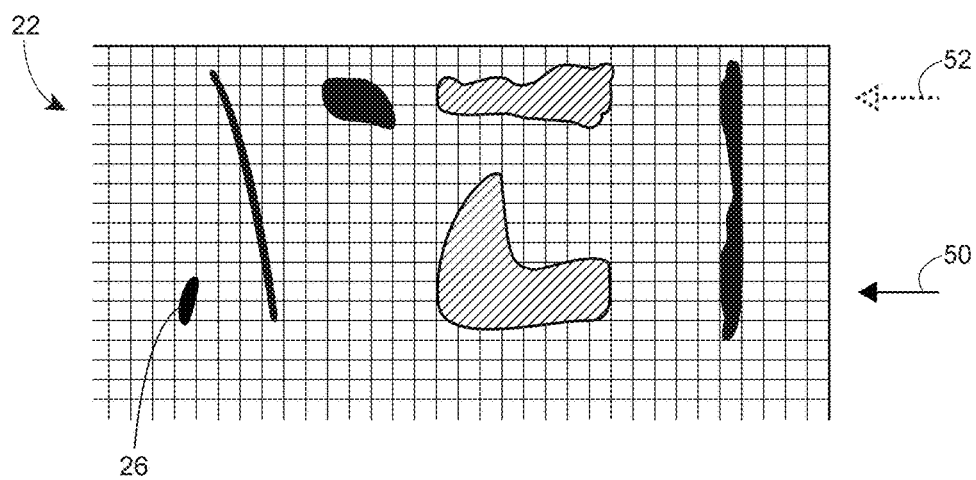
FIG. 4A illustrate portions of an MRI image displayed on a two-dimensional coordinate grid or graph depicting a plurality of virtual paths.
Figure 4B:
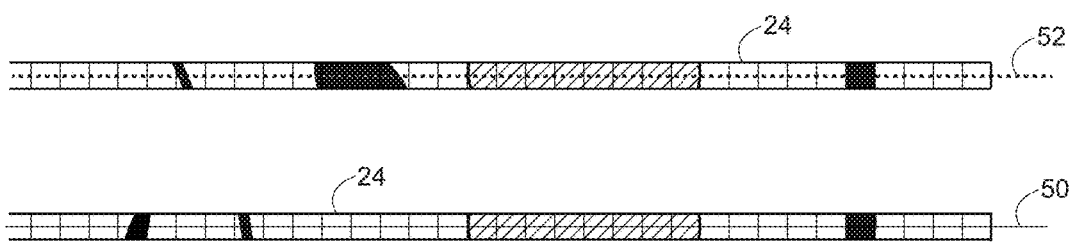
FIG. 4B illustrates two virtual paths of FIG. 4A isolated for comparison of their respective image segments.
Figure 4C:
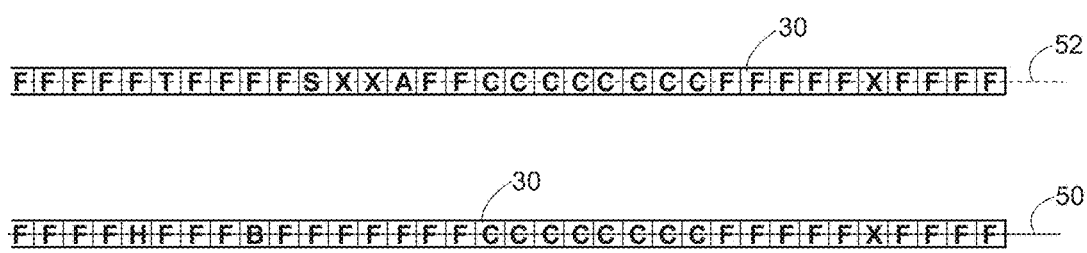
FIG. 4C illustrates the two virtual paths of FIG. 4B wherein their respective image segments have been transformed into electrophysiological value segments.

One example implementation to calculate an alternate physical path is now described with reference to FIGS. 3 and 4A-4C. A selected virtual path to the virtual target 26 is illustrated in the image of FIG. 3. The virtual path shown in FIG. 3, along with several other nearby virtual paths 22 that were defined by the processor, are displayed in a two dimensional image plane shown in FIG. 4A. Each of the virtual paths 22 includes a sequence of image segments 24 that correspond to the various regions in the image of the brain traversed by the virtual path. The image segments 24 may be any size or shape and include pixels, voxels, etc., and are depicted in FIGS. 4A and 4B as two-dimensional squares in this example. Each image segment 24 is correlated by the processor into an electrophysiological value segment 30 shown in FIG. 4C. In particular, the shaded or colored image segments 24 are transformed into electrophysiological values related to the level of neural activity of the associated region of the brain. For example, a dark region on the image of the brain indicates a relatively high level of neural activity and is transformed by the processor to a first electrophysiological value, e.g., X; and a light region on the image of the brain indicates a relatively lesser level of neural activity and is transformed by the processor into a second electrophysiological value, e.g., F. The regions on the brain image having a shade or hue between the dark and light regions, for example, a lined region on the image, indicates a level of neural activity between the dark and light regions and is transformed by the processor to an electrophysiological value that would fall between the electrophysiological values of the dark and light regions, e.g., C, A, S, B, T.

In general, as the microelectrode is extended from the entry point into the skull towards the physical target, the processor receives or picks up, via the microelectrode, electrophysiological signals within the brain. By matching the electrophysiological signals received by the microelectrode to the sequence of electrophysiological value segments of the plurality of virtual paths, the processor is able to calculate the likelihood that the microelectrode will reach the intended physical target. For example, if it is determined that the physical path the microelectrode is travelling coincides with a virtual path that reaches the virtual target, the microelectrode will reach the physical target. If however it is determined that the microelectrode is not on track to reach the physical target, the processor is able to calculate an amount and direction needed to move the microelectrode to an alternate physical path that will reach the physiological target location.

As illustrated on the plane of FIG. 4A, the plurality of virtual paths 22 extend from the outer portion of the image of the brain where the microelectrode would enter the skull and extend toward the virtual target 26. The virtual paths 22 depicted in FIG. 4A are shown essentially parallel to each other, however it is to be understood that the virtual paths need not be parallel, and may intersect or converge, e.g., radial paths, and reach a common location, preferably the virtual target 26. A virtual path 50 that reaches the virtual target is selected and indicated by a solid arrow. The selected virtual path 50 is correlated by the processor into a planned physical path for the microelectrode to travel toward a corresponding physical target. If the brain moves when the skull is opened to receive the microelectrode, the location of the planned physical path within the brain may move, and thus the relationship between the selected virtual path 50 on the image and the corresponding planned physical path in the brain may likely change.

For example, if the brain moved or shifted downward when the skull was opened, the fixed entry point external to the skull that was initially aligned with the planned physical path would appear to have moved or shifted upward. Because the brain has moved downward from its initial position in this example, the microelectrode will actually be extended along a physical path that is relatively above the planned physical path. The "actual" physical path will likely correspond to an "actual" virtual path 52 that is relatively above the initially selected virtual path 50 as indicated by the dotted arrow in FIG. 4A.

The "planned" 50 and "actual" 52 virtual paths corresponding to the "planned" and "actual" physical paths are comparatively shown in FIG. 4B. The sequence of electrophysiological value segments 30 that were transformed from the respective virtual paths 50, 52 by the processor are comparatively shown in FIG. 4C. By inspection of these two virtual paths 50, 52, it can be readily seen that the first twenty electrophysiological value segments 30 of each virtual path are the same and it would therefore be expected that the electrophysiological signals 30 received or picked up by the microelectrode along either corresponding physical path would match either virtual path 50, 52 up to the twentieth segment. At this point therefore, the location of the microelectrode may appear to the processor as being aligned with two possible physical paths, which correspond to virtual paths 50, 52. A further extension of the microelectrode probe into the brain along the "actual" physical path, which corresponds to the actual virtual path 52, encounters an electrophysiological signal that is different than the electrophysiological signal expected to be received by the microelectrode if travelling along the initially planned physical trajectory, which corresponds to planned virtual path 50. At approximately this location along the actual physical path, the processor may become aware that the microelectrode appears not to be travelling along the planned physical path to the physical target. However, because the processor is aware of the electrophysiological value segments 30 of the nearby virtual paths 22, the processor may calculate which particular virtual path of the defined virtual paths the microelectrode is aligned with, i.e., virtual path 52. Because the processor is aware of the spatial difference among all of the defined virtual paths, the processor may then calculate the spatial difference between the planned and actual virtual paths 50, 52 and determine the spatial adjustments to align the microelectrode to the physical target.

After determining the necessary spatial adjustment for the microelectrode, the processor may issue instructions to retract the microelectrode probe from the brain, adjust the entry point of the microelectrode according to the determined spatial difference between the initially planned physical path and a calculated alternate path, and then extend the microelectrode toward the physical target along the alternate path.

Although the above example was presented in a two-dimensional analysis, it is to be understood that the neural targeting system disclosed herein is capable of determining and adjusting for spatial relationships in three dimensions. In particular, the segments of the virtual paths may include three-dimensional voxels integrated from one or more three-dimensional MRI images.

Figure 5:
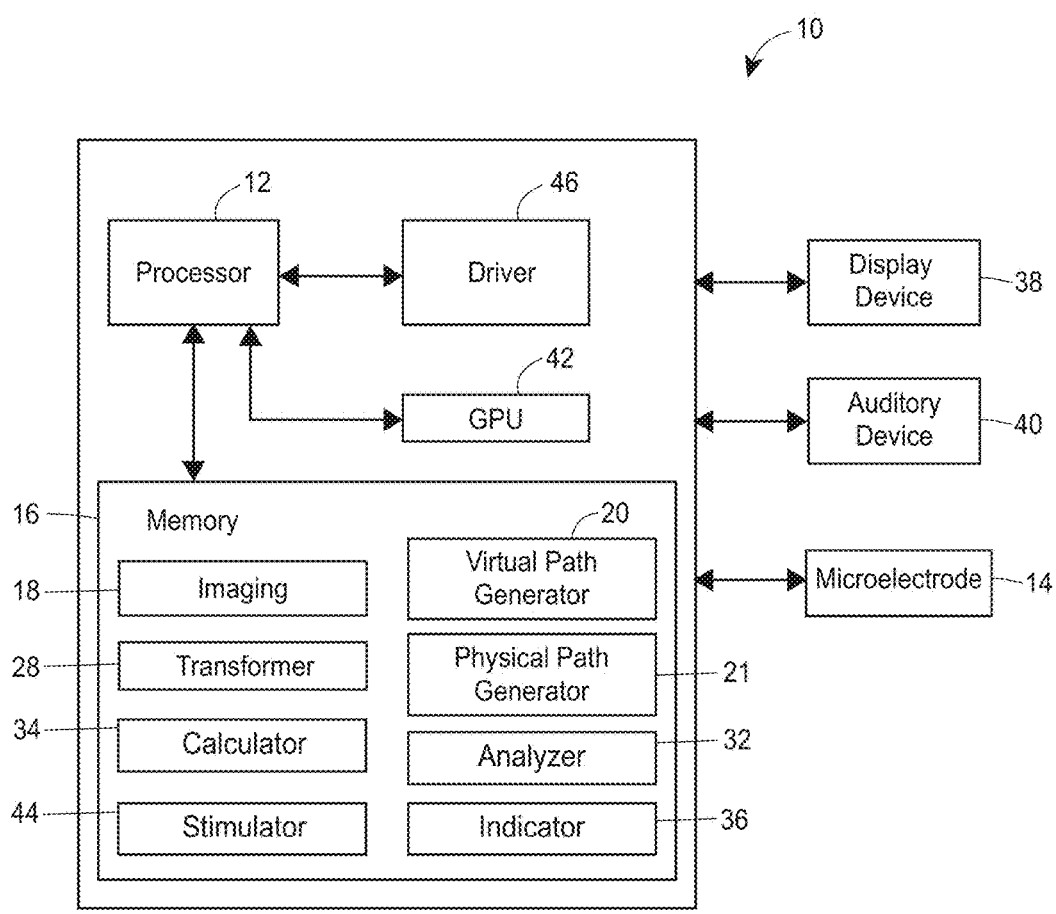
FIG. 5 is block diagram of an example neural targeting system assembled in accordance with the teachings of the present invention and used to target a location within the brain.

FIG. 5 is a block diagram of one example neural targeting system capable of executing the example methods for targeting a location within a brain described herein. In general, hardware designed for neural signal capture is integrated with three-dimensional MRI images rendered in real-time in an intraoperative data acquisition system (IODA). In particular, a targeting system 10 includes one or more processors 12 and a microelectrode 14 operatively coupled to the processor 12. The processor 12 is capable of processing signals, for example, electrophysiological signals, picked up or received by the microelectrode 14 via a wideband low-noise amplifier. The wideband low-noise amplifier may include differential amplifying capabilities, for example: a wideband range of 0 Hz to 10 kHz, and a signal gain per channel 1 to 100,000; a data acquisition card including 1 to 12 channel high impedance analog inputs, a digital converter to USB interface, and a variable sampling frequency between 1 Hz to 50 kHz. To facilitate low-noise recording and wideband signal analysis, the size and material properties of the microelectrode probe 14 may include a tip diameter between 40-100 μm or smaller, and an impedance between 1 kOhm and 1 MOhm or lower, for example. A shielded cable (not shown) may interface with microelectrode 14 and an analog input to an amplifier to provide shielding against stray interference from other electronic hardware and to protect low amplitude raw signals received or captured by the microelectrode 14.

A memory 16 is operatively coupled to the targeting system 10 and is capable of storing several modules or routines, which when executed on the processor 12 may perform at least one step in locating a target within the brain. Some example modules include, and are not limited to: an imaging module 18, a virtual path generator module 20, a physical path generator module 21, a transformer module 28, an analyzer module 32, a calculator module 34, and an indicator module 36.

The imaging module 18 defines an image of the brain into a plurality of image segments 24 wherein each image segment includes a shade or color corresponding to a neural activity or function. For example, darker regions in the image of the brain correspond to more neural activity than lighter regions. The image segments may be any shape, size, or dimension.

The virtual path generator module 20 is used with the processor 12 and defines a plurality of virtual paths 22 through the image of the brain, wherein each virtual path of the plurality of virtual paths includes a sequence of image segments 24 and at least one virtual path of the plurality of virtual paths extends to a virtual target 26. The physical path generator module 21 is used by the processor 12 to correlate a physical path into the brain from a selected virtual path, wherein the microelectrode 14 is extended along the physical path to the physical target.

The transformer module 28 is used with the processor 12 to transform the sequence of the image segments 24 of at least one virtual path 22 of the plurality of virtual paths into a sequence of electrophysiological value segments 30. Each electrophysiological value segment 30 is correlated from an image segment 24 and relates to the value of the neural activity associated with the image.

The analyzer routine 32 analyzes a sequence of electrophysiological signals received by the microelectrode 14 on the physical path to the sequence of electrophysiological value segments 30 of a particular virtual path of the plurality of virtual paths.

The calculator module 34 utilizes the analyzed electrophysiological signals received by the microelectrode 14 on the physical path to the sequences of electrophysiological value segments 30 of the particular virtual path to determine a location of the microelectrode 14 within the brain.

The indicator module 36 indicates the location of the microelectrode 14 in the brain. The indicator module 36 may include a display device 38 that is operatively coupled to the targeting system 10 and responsive to the indicating module 36 for visually indicating the location of the microelectrode 14 in the brain on the MRI image. The indicator module 36 may include an auditory device 40 operatively coupled to the targeting system 10 and responsive to the indicator module 36 for audibly indicating the location of the microelectrode 14.

The targeting system 10 may also include a stimulator module 44 operatively coupled to the processor 12 for generating an intraoperative neurostimulation via the microelectrode 14 to facilitate identifying regions of the brain structure that have an observable response to stimulation in the form of sensations experienced by the individual. The ability to apply stimulation in the operating room is an effective technique to quickly determine if the position of the probe is suitable to mitigate disease symptoms. In addition, the targeting system 10 may be modified for specific types of DBS surgeries, e.g., essential tremor, wherein custom printed circuit boards (PCBs) may facilitate simultaneous microstimulation and microelectrode recording. This additional functionality provides the targeting system 10 with the ability to explore the most effective and efficient stimulation necessary for each individual patient. The targeting system 10 can also apply stimulation via the stimulator module 44 with custom parameters, including: custom waveform(s), variable frequency, variable signal pulse width, and high precision signal amplitude. The stimulation may be based on a calculated optimized stimulation amplitude and applied with constant current, which has been shown to offer better control of applied energy into brain tissue compared to other available devices that use voltage controlled stimulation. In one embodiment, the stimulator module 44 may include a constant current stimulator including a voltage following stimulator with controllable current output based on probe impedance (i.e., 1V=1 mA with 1 kOhm impedance probe, or 1V=10 μA with 1 MOhm probe impedance). In another implementation of the example targeting system, an automated microelectrode probe driver 46 may be integrated into the design to advance and retract the microelectrode 14. The driver 46 may include ultra-quiet vibration control and provide high resolution in-step advancements to enable the user to record extremely precise depth positions for controlled, automated targeting and microelectrode probe advancement into brain tissue.

Figure 6:
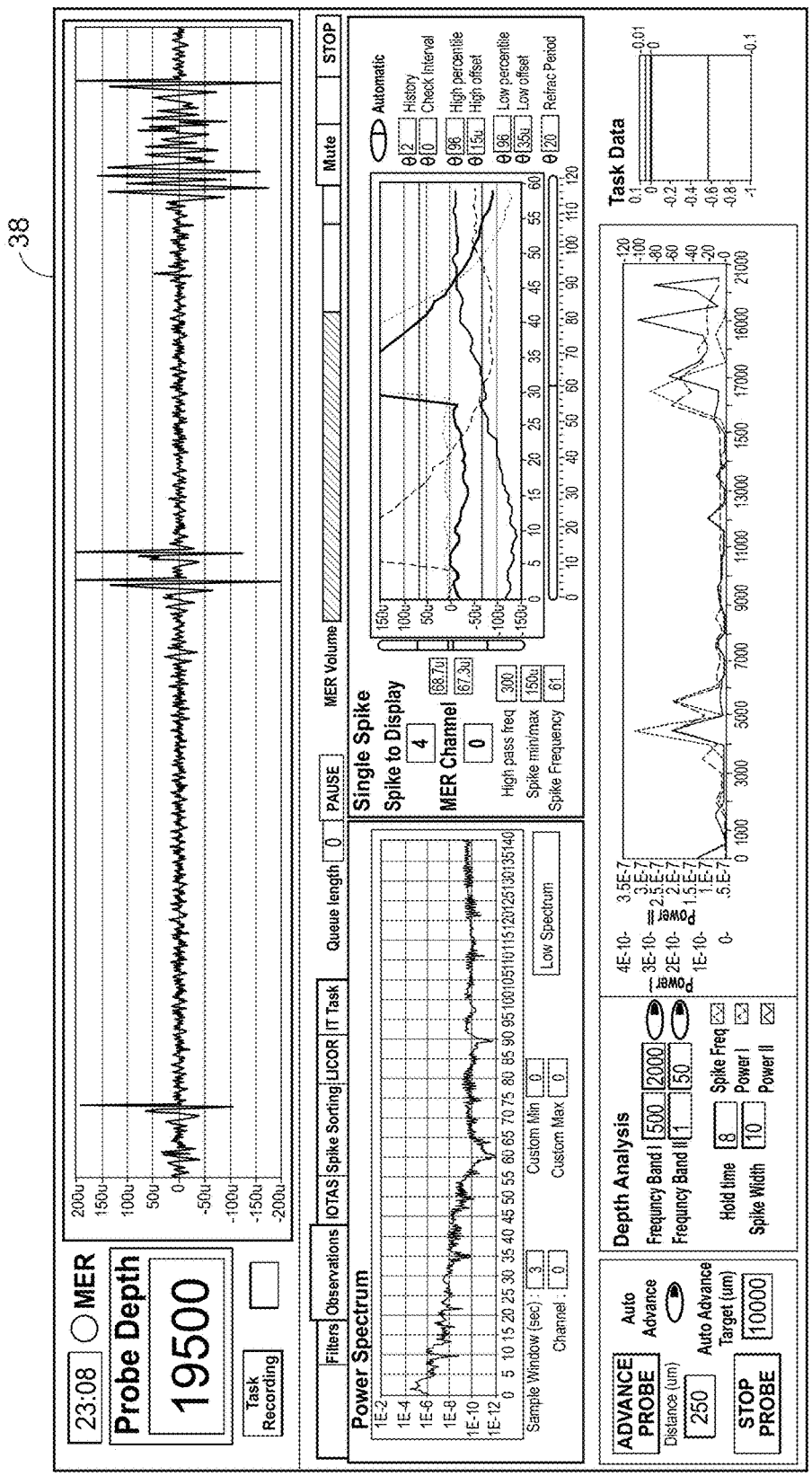
FIG. 6 is an illustration of an example display of raw brain signals received by the microelectrode and displayed on a screen.
Figure 7:
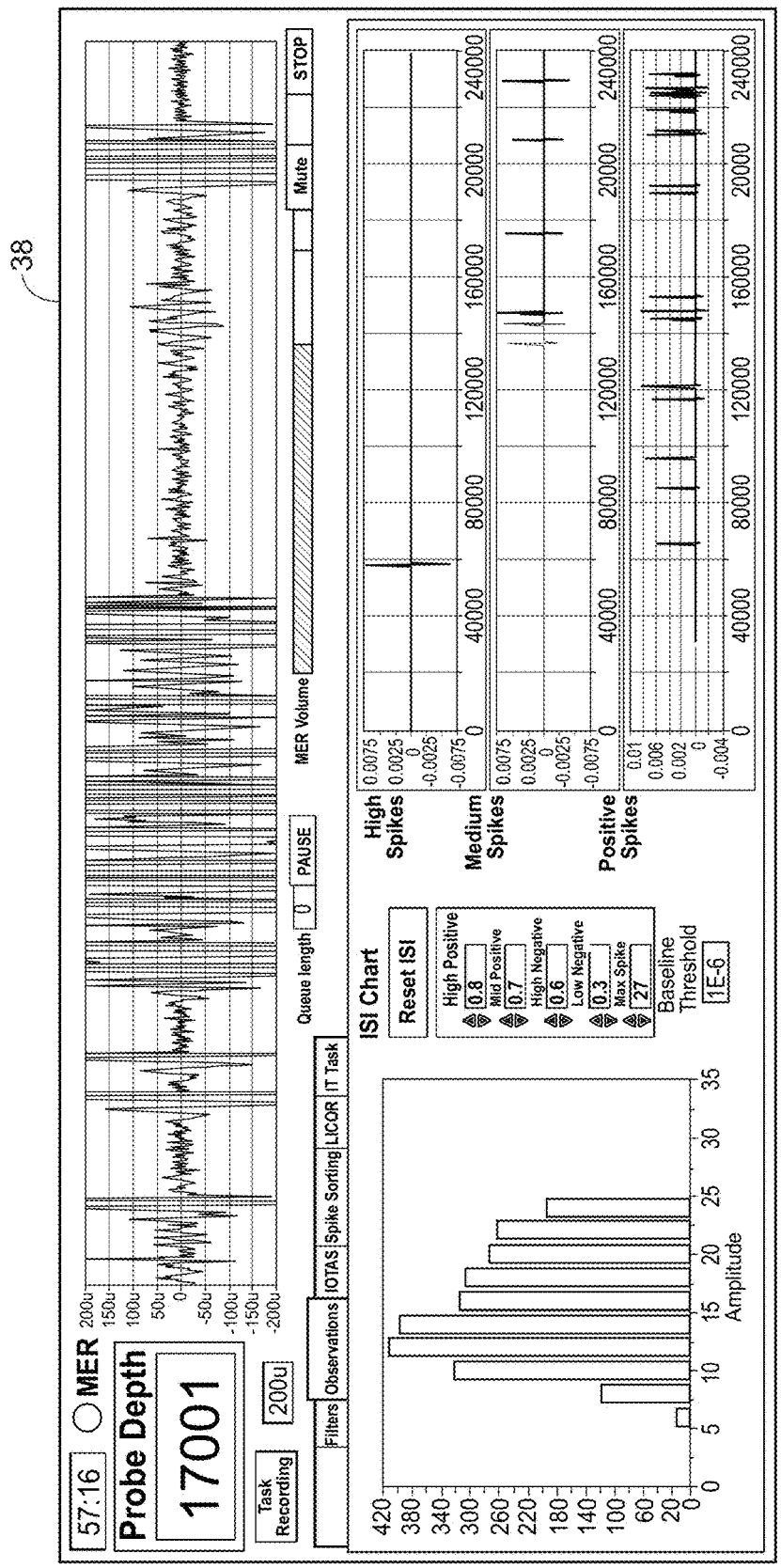
FIG. 7 is an illustration of another example display of raw brain signals received by the microelectrode and displayed on a screen.

FIGS. 6 and 7 are example displays of information provided by one implementation of the neural targeting system 10 shown on the display device 38. FIG. 6 displays filtered electrophysiological information using an adjustable frequency bandwidth (300 Hz-5 Khz) display for single spike visualizing. Also included in FIG. 6 is a display of single spike information with an auto-thresholding feature, auto-probe advancing, data writing, auto-spike sorting, power spectrum of signal, single spike display, depth vs. power analysis with an adjustable frequency view, digital control of the microelectrode advancement motor, and volume control for the electrophysiological audio analysis. In FIG. 7, a full bandwidth signal (1 Hz-8 kHz) is displayed as well as an illustration of auto-spike sorting analysis defining different spike types from a static depth, and an inter-spike-interval histogram displaying the amplitude and amount of recorded spikes and count.

Figure 8:
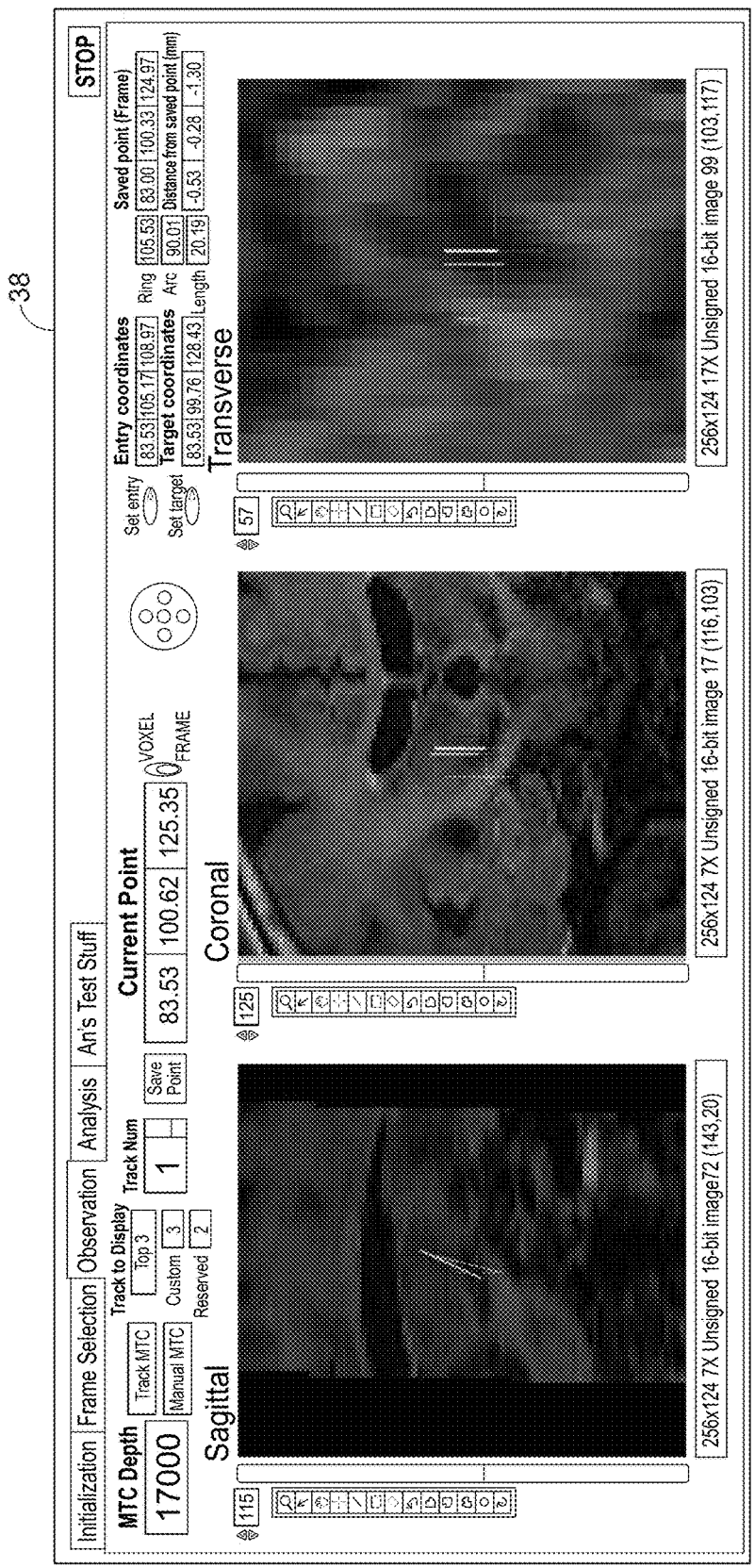
FIG. 8 is an illustration of a microelectrode superimposed on a brain image in three views: coronal, sagittal, and transverse; and displayed on a screen.
Figure 9:
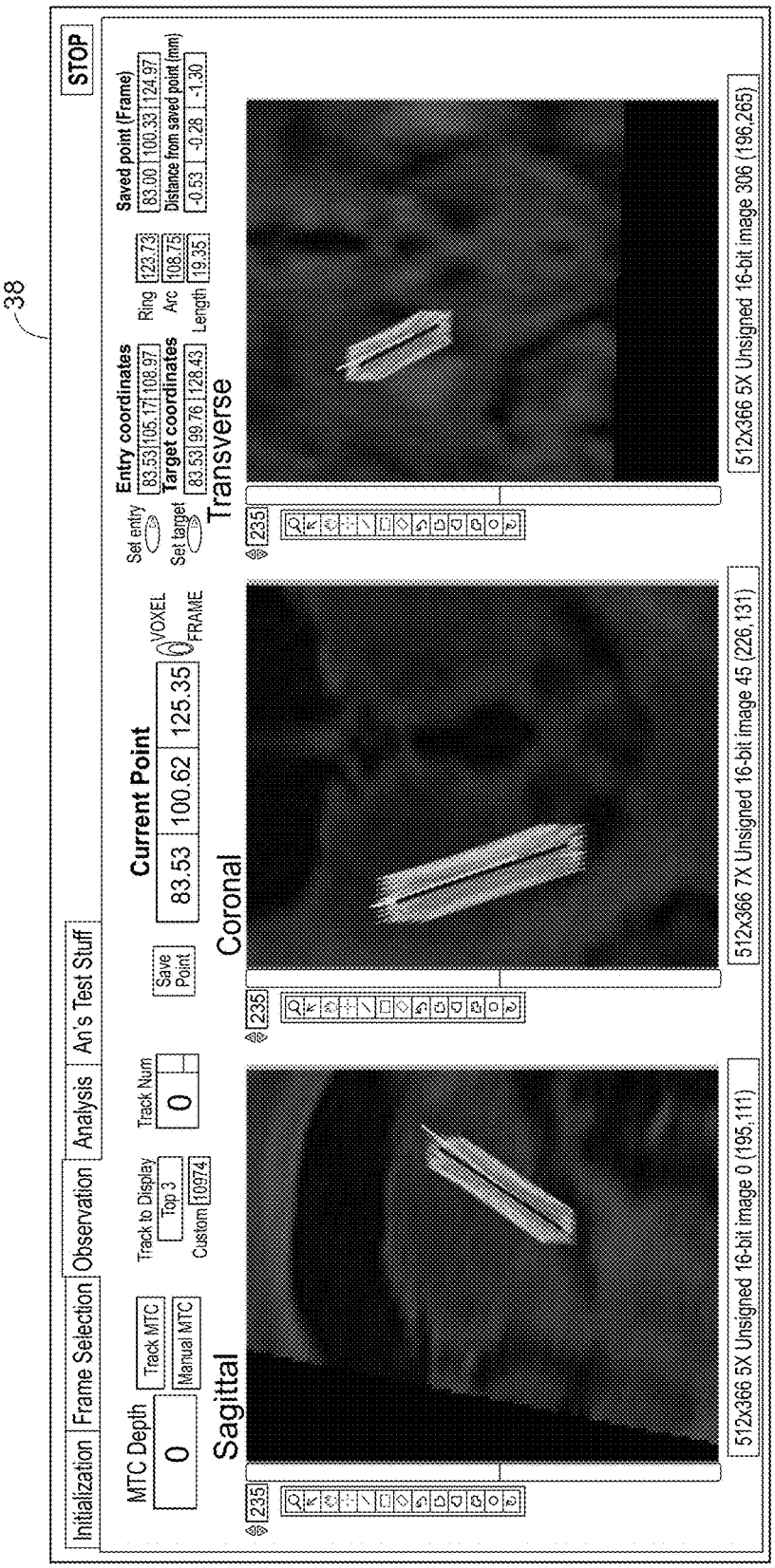
FIG. 9 is an illustration of a plurality of virtual paths for potential travel of the microelectrode superimposed on a brain image in three views: coronal, sagittal, and transverse; and displayed on a screen.

In FIGS. 8 and 9, example images provided by one implementation of the neural targeting system 10 depicts the conversion of voxel image coordinates to physical or frame coordinates via on screen selection of frame fiducials in real-time. An image of the microelectrode 14 is shown superimposed on the image of the brain in three views: sagittal, coronal, and transverse. The system 10 tracks the advancement of the microelectrode 14 in real-time and the microelectrode's current position in the brain is displayed on the brain image. As shown in FIG. 9, the neural targeting system 10 is capable of displaying the various potential virtual paths for the probe, e.g., in amount, such as the top 3, 5, 10; or percentage, such as the top 1%, 10%, 20% of all potential virtual path trajectories. The user is also able to select the target, entry point(s), and ring and arc angle for the microelectrode 14.

Figure 10:
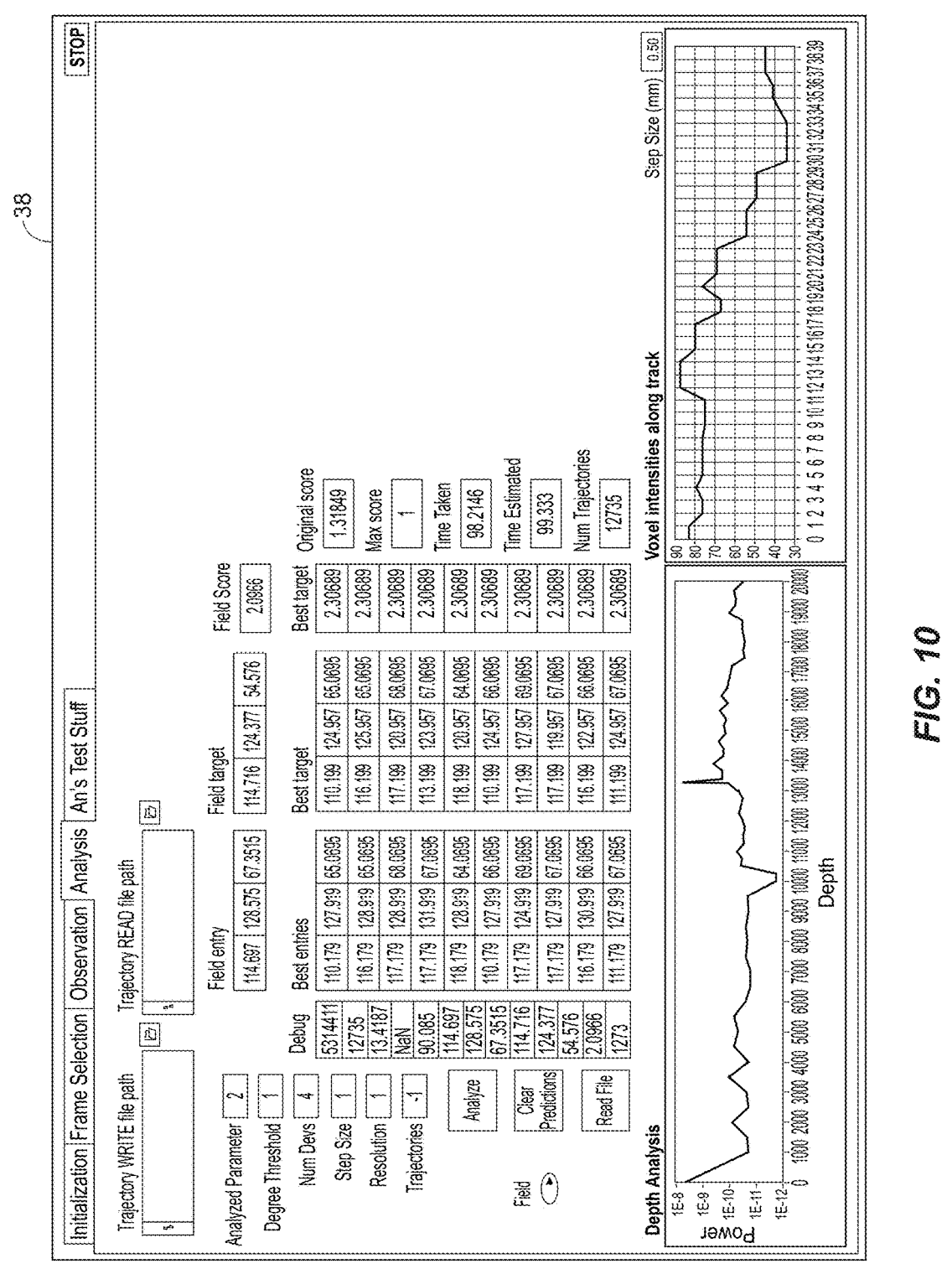

Referring now to FIG. 10, example depth and voxel intensities analyses along a selected virtual path trajectory are illustrated. In particular, the matching of received raw brain signals to voxel values (e.g., electrophysiological value segments 30 transformed from the image segments 24 of the brain) along the planned trajectory of the microelectrode and the calculated line of voxels that most likely matches the electrophysiological pattern of the raw brain signal and displays this on the same brain image. Directional changes to move the microelectrode to achieve the intended planned target point are provided to the user. The user is able to select parameters for analysis and the top entry and target coordinates may be displayed.

Figure 11:
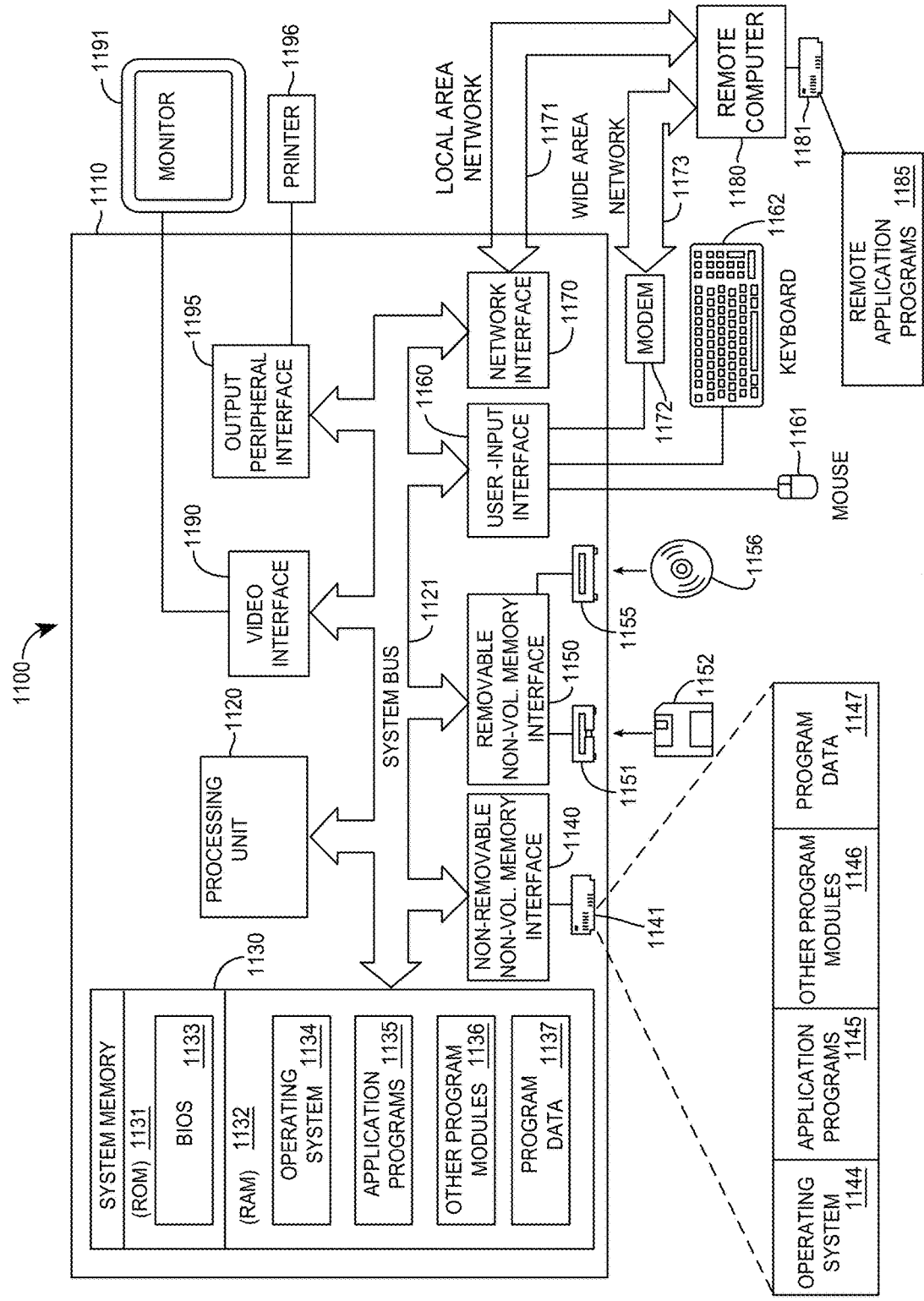
FIG. 11 illustrates an exemplary block diagram of another embodiment of neural targeting system assembled in accordance with the teachings of the present invention and used to locate a target in the brain.

FIG. 11 illustrates an exemplary block diagram of a computer system 1100 on which an exemplary method for targeting a brain location for DBS may operate in accordance with the example embodiments described herein. The computer system 1100 of FIG. 11 includes a computing device in the form of a computer 1110. Components of the computer 1110 may include, but are not limited to, a processing unit 1120, a system memory 1130, and a system bus 1121 that couples various system components including the system memory to the processing unit 1120. The system bus 1121 may be any of several types of bus structures including a memory bus or memory controller, a peripheral bus, and a local bus using any of a variety of bus architectures. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 1110 typically includes a variety of computer readable media. Computer readable media can be any available media that can be accessed by the computer 1110 and includes both volatile and nonvolatile media, and both removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by the computer 1110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above are also included within the scope of computer readable media.

The system memory 1130 includes computer storage media in the form of volatile and/or nonvolatile memory such as read only memory (ROM) 1131 and random access memory (RAM) 1132. A basic input/output system 1133 (BIOS), containing the basic routines that help to transfer information between elements within the computer 1110, such as during start-up, is typically stored in ROM 1131. RAM 1132 typically contains data and/or program modules that are immediately accessible to and/or presently being operated on by the processing unit 1120. By way of example, and not limitation, FIG. 11 illustrates operating system 1134, application programs 1135, other program modules 1136, and program data 1137.

The computer 1110 may also include other removable/non-removable, volatile/nonvolatile computer storage media. By way of example only, FIG. 11 illustrates a hard disk drive 1141 that reads from or writes to non-removable, nonvolatile magnetic media, a magnetic disk drive 1151 that reads from or writes to a removable, nonvolatile magnetic disk 1152, and an optical disk drive 1155 that reads from or writes to a removable, nonvolatile optical disk 1156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1141 is typically connected to the system bus 1121 through a non-removable memory interface such as interface 1140, and magnetic disk drive 1151 and optical disk drive 1155 are typically connected to the system bus 1121 by a removable memory interface, such as interface 1150.

The drives and their associated computer storage media discussed above and illustrated in FIG. 11 provide storage of computer readable instructions, data structures, program modules and other data for the computer 1110. In FIG. 11, for example, hard disk drive 1141 is illustrated as storing operating system 1144, application programs 1145, other program modules 1146, and program data 1147. Note that these components can either be the same as or different from operating system 1134, application programs 1135, other program modules 1136, and program data 1137. Operating system 1144, application programs 1145, other program modules 1146, and program data 1147 are given different numbers here to illustrate that, at a minimum, they are different copies. A user may enter commands and information into the computer 1110 through input devices such as a keyboard 1162 and cursor control device 1161, commonly referred to as a mouse, trackball or touch pad. A monitor 1191 or other type of display device is also connected to the system bus 1121 via an interface, such as a graphics controller 1190. In addition to the monitor, computers may also include other peripheral output devices such as printer 1196, which may be connected through an output peripheral interface 1195.

The computer 1110 may operate in a networked environment using logical connections to one or more remote computers, such as a remote computer 1180. The remote computer 1180 may be a personal computer, a server, a router, a network PC, a peer device or other common network node, and typically includes many or all of the elements described above relative to the computer 1110, although only a memory storage device 1181 has been illustrated in FIG. 11. The logical connections depicted in FIG. 11 include a local area network (LAN) 1171 and a wide area network (WAN) 1173, but may also include other networks. Such networking environments are commonplace in hospitals, medical centers, enterprise-wide computer networks, intranets and the Internet.

When used in a LAN networking environment, the computer 1110 is connected to the LAN 1171 through a network interface or adapter 1170. When used in a WAN networking environment, the computer 1110 typically includes a modem 1172 or other means for establishing communications over the WAN 1173, such as the Internet. The modem 1172, which may be internal or external, may be connected to the system bus 1121 via the input interface 1160, or other appropriate mechanism. In a networked environment, program modules depicted relative to the computer 1110, or portions thereof, may be stored in the remote memory storage device 1181. By way of example, and not limitation, FIG. 11 illustrates remote application programs 1185 as residing on memory device 1181.

The communications connections 1170, 1172 allow the device to communicate with other devices. The communications connections 1170, 1172 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

The methods for targeting for deep brain stimulation embodiments described above may be implemented in part or in their entirety using one or more computer systems such as the computer system 1100 illustrated in FIG. 11. The image data and/or target location in the image may be received by a computer such as the computer 1110, for example. The image data may be received over a communication medium such as local area network 1171 or wide area network 1173, via network interface 1170 or user-input interface 1160, for example. As another example, the image data and/or target data may be received from a remote source such as the remote computer 1180 where the data is initially stored on memory device such as the memory storage device 1181. As another example, the image data and/or target data may be received from a removable memory source such as the nonvolatile magnetic disk 1152 or the nonvolatile optical disk 1156. As another example, the image data and/or target data may be received as a result of a human entering data through an input device such as the keyboard 1162 or portable memory device.

Some or all calculations performed in the neural targeting embodiments described above (e.g., calculations for determining the position of the microelectrode), may be performed by a computer such as the computer 1110, and more specifically may be performed by a processor such as the processing unit 1120, for example. In some embodiments, some calculations may be performed by a first computer such as the computer 1110 while other calculations may be performed by one or more other computers such as the remote computer 1180. The calculations may be performed according to instructions that are part of a program such as the application programs 1135, the application programs 1145 and/or the remote application programs 1185, for example.

Indicating a target, as described above in the neural targeting system embodiments, may also be performed by a computer such as the computer 1110. The virtual paths may be defined by signal and graphics analyses of the images, e.g., MRI, CT, stored in the ROM memory 1131 and/or the RAM memory 1132, for example. In some embodiments, indicating the target may include sending data over a network such as the local area network 1171 or the wide area network 1173 to another computer, such as the remote computer 1181. Such networking environments are commonplace in hospitals, medical centers, enterprise-wide computer networks, intranets and the Internet. In other embodiments, indicating a target may include sending data over a video interface such as the video interface 1190 to display information relating virtual paths on an output device such as the monitor 1191, printer 1196, or speaker (not shown), for example.

The example implementations of the targeting system and method described above are capable of providing real-time visual targeting with continuous updates to the actual microelectrode location and trajectory in relation to a static 3D representation of an individual's brain image(s), e.g., MRI image(s). More specifically, the targeting system and method are able to predict and to update the microelectrode position on the visual display and alert the user in advance if the neural signals encountered by the microelectrode are not indicative of the intended trajectory. The targeting system and method are able to determine the exact amount and direction needed to move the microelectrode in order to successfully hit the physiologic target location in the brain. Thus, the targeting system and method may significantly reduce the amount of time associated with targeting and provide a more reliable, accurate, and automated method for DBS surgery, which may reduce surgical error and lower the barrier to entry for interested neurosurgeons.

What is claimed:

1. A method for targeting a location within a brain for deep brain stimulation, or other types of brain surgeries requiring targeting, the method comprising:

identifying a virtual target within an image of the brain, the image including a plurality of regions, each region including a hue corresponding to an electrophysiological value;

defining, via a processor, a portion of the image into a plurality of virtual paths, each virtual path of the plurality of virtual paths including a sequence of image segments and at least one virtual path of the plurality of virtual paths extending to the virtual target;

correlating, via the processor, each image segment of the sequences of image segments of the plurality of virtual paths into an electrophysiological value segment, thereby transforming the sequence of image segments of each virtual path into a sequence of electrophysiological value segments;

correlating the virtual target within the image to a physical target in the brain; selecting one of the at least one virtual path of the plurality of virtual paths that extends to the virtual target; correlating the selected one virtual path to a physical path in the brain;

extending a microelectrode into the brain on the physical path toward the physical target, wherein extending the microelectrode is performed manually and/or by a robotic device;

receiving, via the microelectrode, a sequence of electrophysiological signals as the microelectrode extends on the physical path toward the physical target;

and comparing, via the processor, the sequence of electrophysiological signals received by the microelectrode on the physical path to the sequence of electrophysiological value segments of the selected one virtual path of the plurality of virtual paths, wherein when the received sequence of electrophysiological signals matches the electrophysiological value segments of the selected one virtual path of the plurality of virtual paths, continuing to extend the microelectrode on the physical path, and when the received sequence of electrophysiological signals does not match the electrophysiological value segments of the selected one virtual path of the plurality of virtual paths, withdrawing the microelectrode from the brain, comparing the received sequence of electrophysiological signals to the sequence of electrophysiological value segments of the plurality of defined virtual paths, selecting an alternate virtual path from among the defined virtual paths that includes the sequence of electrophysiological value segments that matches the sequence of electrophysiological signals received by the microelectrode, calculating a spatial distance between the selected one virtual path and the selected alternate virtual path, calculating an alternate physical path to the physical target based on the calculated spatial distance, and extending the microelectrode into the brain on the calculated alternate physical path.

2. The method of claim 1, further comprising calculating, via a processor, a physical location of the microelectrode in the brain with respect to the physical target.

3. The method of claim 2, further comprising advancing the microelectrode further toward the physical target if the physical location of the microelectrode is determined to be on the physical path to reach the physical target.

4. The method of claim 2, further comprising planning, via a processor, an alternate physical path for the microelectrode to the physical target if the physical location of the microelectrode is determined to be off the physical path to reach the physical target.

5. The method of claim 2, further comprising indicating, via a processor, the physical location of the microelectrode.

6. The method of claim 5, wherein indicating the physical location of the microelectrode includes displaying a visual indicator.

7. The method of claim 6, wherein displaying a visual indicator includes displaying a virtual location of the microelectrode on the image of the brain, wherein the virtual location of the microelectrode on the image of the brain corresponds to the physical location of the microelectrode in the brain.

8. The method of claim 5, wherein indicating the physical location of the microelectrode includes emitting an auditory indicator.

9. The method of claim 1, further comprising generating, via a processor, a current stimulation of the microelectrode based on calculated optimized stimulation amplitude.

10. A system for targeting a location within a brain for deep brain stimulation, or other types of brain surgeries requiring targeting, the system comprising:

an integrated monitoring system including one or more processors and a microelectrode operatively coupled to the one or more processors, wherein the microelectrode senses physiological signals of the brain;

a memory operatively coupled to the integrated monitoring system, the memory storing instructions that when executed by the one or more processors, cause the system to:

define an image of the brain into a plurality of image segments with each image segment including a hue corresponding to an electrophysiological value;

define a plurality of virtual paths through the image, each virtual path of the plurality of virtual paths including a sequence of the image segments and at least one virtual path of the plurality of virtual paths extends to a virtual target;

transform the sequences of the image segments of each virtual path of the plurality of virtual paths into a sequence of electrophysiological value segments;

correlate the virtual target within the image to a physical target in the brain;

select one of the at least one virtual path of the plurality of virtual paths that extends to the virtual target;

correlate the selected one virtual path to a physical path in the brain;

extend a microelectrode into the brain on the physical path toward the physical target, which may be performed manually or automatically using a robot or robotic system; receive, via the microelectrode, a sequence of electrophysiological signals as the microelectrode extends on the physical path toward the physical target;

analyze the sequence of electrophysiological signals received by the microelectrode on the physical path, wherein when the received sequence of electrophysiological signals matches the electrophysiological value segments of the selected one virtual path of the plurality of virtual paths, continue to extend the microelectrode on the physical path, and when the received sequence of electrophysiological signals does not match the electrophysiological value segments of the selected one virtual path of the plurality of virtual paths, withdraw the microelectrode from the brain, compare the received sequence of electrophysiological signals to the sequence of electrophysiological value segments of the plurality of defined virtual paths, select an alternate virtual path from among the defined plurality of virtual paths that includes the sequence of electrophysiological value segments that matches the sequence of electrophysiological signals received by the microelectrode, calculate a spatial distance between the selected one virtual path and the selected alternate virtual path, calculate an alternate physical path to the physical target based on the calculated spatial distance, and extend the microelectrode into the brain on the calculated alternate physical path.

11. The system of claim 10, further comprising a display device operatively coupled to the integrated monitoring system and responsive to the one or more processors for visually indicating the location of the microelectrode.

12. The system of claim 10, further comprising an auditory device operatively coupled to the integrated monitoring system and responsive to the one or more processors for audibly indicating the location of the microelectrode.

13. The system of claim 10, further comprising a stimulator operatively coupled to the one or more processors for generating a current stimulation of the microelectrode based on calculated optimized stimulation amplitude.

14. The system of claim 10, further comprising a robot or robotic system operatively coupled to the one or more processors for extending the microelectrode into the brain.

15. A tangible non-transitory computer-readable storage medium having computer-readable instructions stored there on that, when executed on by one or more processors of a system for targeting a location in a brain for deep brain stimulation or other types of brain surgeries requiring targeting, cause the one or more processors to:
- identify a virtual target within an image of the brain, the image including a plurality of regions, each region including a hue corresponding to an electrophysiological value;
- define a portion of the image into a plurality of virtual paths, each virtual path of the plurality of virtual paths including a sequence of image segments and at least one virtual path of the plurality of virtual paths extends to the virtual target;
- transform each image segment of the sequence of image segments of the plurality of virtual paths into an electrophysiological value segment;
- correlate the virtual target within the image to a physical target in the brain;
- select one of the at least one virtual path of the plurality of virtual paths that extends to the virtual target;
- correlate the selected one virtual path to a physical path in the brain;
- extend a microelectrode into the brain on the physical path toward the physical target, which may be performed manually or automatically using a robot or robotic system;
- receive, via the microelectrode, a sequence of electrophysiological signals as the microelectrode extends on the physical path toward the physical target;
- compare the sequence of electrophysiological signals received on the physical path by the microelectrode to the sequence of electrophysiological value segments of the selected one virtual path of the plurality of virtual paths, wherein when the received sequence of electrophysiological signals matches the electrophysiological value segments of the selected one virtual path of the plurality of virtual paths, continue to extend the microelectrode on the physical path, and when the received sequence of electrophysiological signals does not match the electrophysiological value segments of the selected one virtual path of the plurality of virtual paths, withdraw the microelectrode from the brain, compare the received sequence of electrophysiological signals to the sequence of electrophysiological value segments of the plurality of defined virtual paths, select an alternate virtual path from among the defined plurality of virtual paths that includes the sequence of electrophysiological value segments that matches the sequence of electrophysiological signals received by the microelectrode, calculate a spatial distance between the selected one virtual path and the selected alternate virtual path, calculate an alternative physical path to the physical target based on the calculated spatial distance, and extend the microelectrode into the brain on the calculated alternate physical path.

16. The tangible non-transitory computer-readable storage medium of claim 15, wherein the computer-readable instructions stored there on cause the one or more processors to calculate a physical location of the microelectrode in the brain with respect to the physical target.

17. The tangible non-transitory computer-readable storage medium of claim 15, wherein the computer-readable instructions stored there on cause the one or more processors to advance the microelectrode further toward the physical target if the physical location of the microelectrode is determined to be on the physical path to reach the physical target.

18. The tangible non-transitory computer-readable storage medium of claim 15, wherein the computer-readable instructions stored there on cause the one or more processors to indicate the physical location of the microelectrode in the brain.

19. The tangible non-transitory computer-readable storage medium of claim 15, wherein indicating the physical location of the microelectrode includes displaying a visual indicator.

20. The tangible non-transitory computer-readable storage medium of claim 15, wherein the computer-readable instructions stored there on cause the one or more processors to generate a current stimulation of the microelectrode based on calculated optimized stimulation amplitude.

* * * * *